United States Patent [19]

Visuri

[11] Patent Number: 5,120,650
[45] Date of Patent: Jun. 9, 1992

[54] METHOD FOR PRODUCING CRYSTALLINE GLUCOSE ISOMERASE

[75] Inventor: Kalevi Visuri, Kantvik, Finland

[73] Assignee: Stabra AG, Zug, Switzerland

[21] Appl. No.: 421,137

[22] Filed: Oct. 13, 1989

[51] Int. Cl.$^5$ .............. C12N 11/14; C12N 11/08; C12N 9/92; C12N 11/12

[52] U.S. Cl. ................... 435/176; 435/179; 435/180; 435/234; 435/803; 435/814; 435/816

[58] Field of Search ............ 435/174, 176, 178, 180, 435/234, 803, 814, 816

[56] References Cited

U.S. PATENT DOCUMENTS 4,237,231 12/1980 Jackson et al. .................. 435/234

4,699,882 10/1987 Visuri ............................ 435/188 X

Primary Examiner—David M. Naff
Attorney, Agent, or Firm—James G. Passe

[57] ABSTRACT

In a process for growing enzyme crystals, small crystals are continuously removed from a crystallizer, dissolved and returned to the crystallizer to maintain a supersaturated state. The method permits the growing of large crystalline enzymes of uniform size of about 0.5 to 1 mm. Solid materials can be coated with crystalline enzymes by placing a solid material in the crystallizer such that crystals deposit on the solid material. The process is preferably used to produce crystalline glucose isomerase.

24 Claims, 3 Drawing Sheets

METHOD FOR PRODUCING CRYSTALLINE GLUCOSE ISOMERASE

BACKGROUND OF THE INVENTION

Extensive literature exists that describes how to make large, single crystals of proteins and enzymes for research purposes such as for x-ray crystallography. The principle of most of these methods is to concentrate the enzyme very slowly during the course of several days, weeks or even months by evaporation of water from the sample. A review of these methods can be found in Journal of Crystal Growth, Volume 90 (1988), pages 1-368, which describes many of the methods and approaches considered to be of value when crystallizing biological macromolecules. None of the known methods is, however, useful for preparative or industrial scale production of large uniform crystals of enzymes.

There is a wealth of literature and knowledge on the crystallization of small molecular organic and inorganic compounds. For many small molecular compounds, it is well known how to produce large uniform crystals in evaporation or cooling batch crystallization. There are numerous methods to selectively remove small crystals from a crystallizer and thereafter collect the desired large size class of crystals. Usually the procedures include methods to maintain some degree of supersaturation until the desired size of crystals is obtained Despite the wide theoretical and practical knowledge of crystallization in general, however, the crystal growth processes that sort crystals based on size and enable production of large crystals have not been applied on the more than 1025 examples of crystallizations of biological macromolecules (G. L. Gilliland: A biological macromolecule crystallization database: a basis for a crystallization strategy. Journal of Crystal Growth vol. 90 (1988) 51-59.).

An industrial scale batch crystallization process for glucose isomerase is described in U.S. Pat. No. 4,699,882. In this method, the enzyme is crystallized in a suitable concentration of ammonium sulfate. The crystals produced are of varying size, typically 1 to 100 micrometers, and there is no control of size distribution or average size. The method is suitable for large scale production, but it is not useful for the production of large, for example, 0.5 to 1 mm crystals, or for the crystallization of such large crystals on the surface of solid inert materials.

It is therefore an object of the invention to enable an industrial scale procedure for making large enzyme crystals. Such crystals provide several advantages in that they can be used directly in columns (if they are insoluble in the substrate), and they avoid clogging or flow resistance problems that would be obtained with small crystals. In addition, enzymes produced as large crystals can be separated more easily from other materials (impurities), including solid, small particular debris such as amorphous precipitate or cell walls (that are typically 0.1-1 um in size), by screening or sedimentation and centrifugation, thus allowing their production in greater yields.

It is a further object of the invention to provide a method for depositing enzymes as crystalline layers onto surfaces of inert materials whereby the coated material can be used to catalyze specific reactions. The use of foreign materials as nuclei for crystallization provides a novel and surprisingly advantageous method of preparing immobilized enzymes. The method disclosed herein is also very useful for the growth of large enzyme crystal masses on such solid surfaces. By growing large crystals on the surface of solid materials, there is provided a simple method for enzyme recovery, immobilization and use in industrial processes.

SUMMARY OF THE INVENTION

These and other advantages are obtained using crystals or crystal coated solids produced according to the present invention. According to the invention, relatively large enzyme crystals are formed, either as pure individual crystals or as crystalline deposits on solid material. According to one embodiment, a cooled crystal-growing chamber (crystallizer) is loaded with a saturated solution or fine suspension of a crystallizable enzyme. The solution (or suspension) is thereupon cooled to initiate crystallization of enzyme crystals. A portion of the liquid in the chamber is continuously removed, carrying with it a portion of the newly formed crystals in suspension. The liquid is removed through a classifying device, which holds back relatively large crystals and allows only relatively small crystals to pass through. The liquid carrying the relatively small crystals is re-heated so as to dissolve the enzyme crystals, and the dissolved enzyme is returned to the cooled crystal growing chamber where it is again caused to crystallize. The crystallization occurs, at least in part, on the previously formed, relatively large crystals which, through the action of the classifying device, were never permitted to leave the crystal growing chamber. In this manner, the relatively large enzyme crystals are permitted to grow under the continuous action of crystallization, size classification, re-heating and recycling of the enzyme comprising the smaller crystals.

The removal of the enzyme comprising the smaller crystals and its recycling in the dissolved state maintains the liquid environment in the crystal growing chamber in a supersaturated state. The large crystals are harvested (recovered) when they reach the size suitable for their ultimate purpose. In this embodiment, large enzyme crystals ranging in size from 0.5 to 1 millimeter in diameter can be produced. Such enzymes can be continuously collected by conventional means such as sedimentation or centrifugation and used advantageously in industrial scale processes.

In a further embodiment, fixed, loose or free-floating, insoluble, substantially inert materials are placed within the crystallization chamber, wherein a portion of the crystallizing enzyme is deposited on the surface of the material which serves as a nucleus for crystallization. If the solid material in the chamber is fixed, the liquid containing crystals which have not deposited can be continuously removed from the crystallizer without passing through a classifying device. The liquid is heated to dissolve a substantial portion of the enzyme, and it is then put back into the crystallizer, wherein the enzyme is crystallized directly on the surface of the solid material, thus building up the crystalline layer. If the solid material(s) to be coated consists of freely floating particles, a classifying device such as a screen may be necessary to keep the particles in the crystallizer while the other non-deposited crystals are removed, re-dissolved and returned to the chamber as before. In either embodiment using an inert material the surface of the material can be coated in as thick a layer as desired, as long as a state of supersaturation is maintained in the crystallizer. In the preferred embodiment, once the enzyme is deposited, it is fixed to the solid material by crosslinking with an agent such as glutaraldehyde.

DETAILED DESCRIPTION OF THE INVENTION

Figure 1:
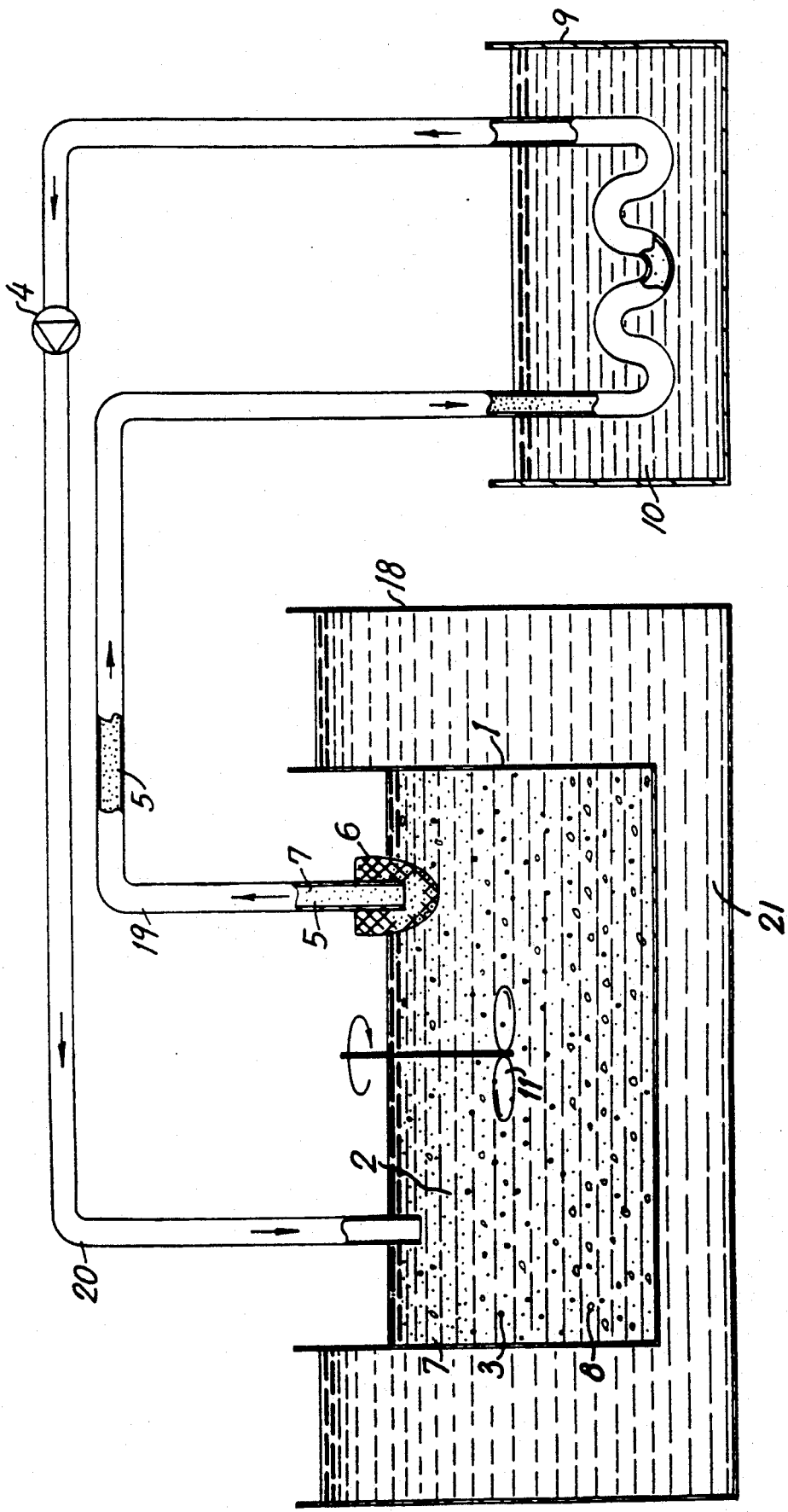
FIG. 1 is a schematic diagram reflecting one embodiment of the process of the invention.
Figure 2:
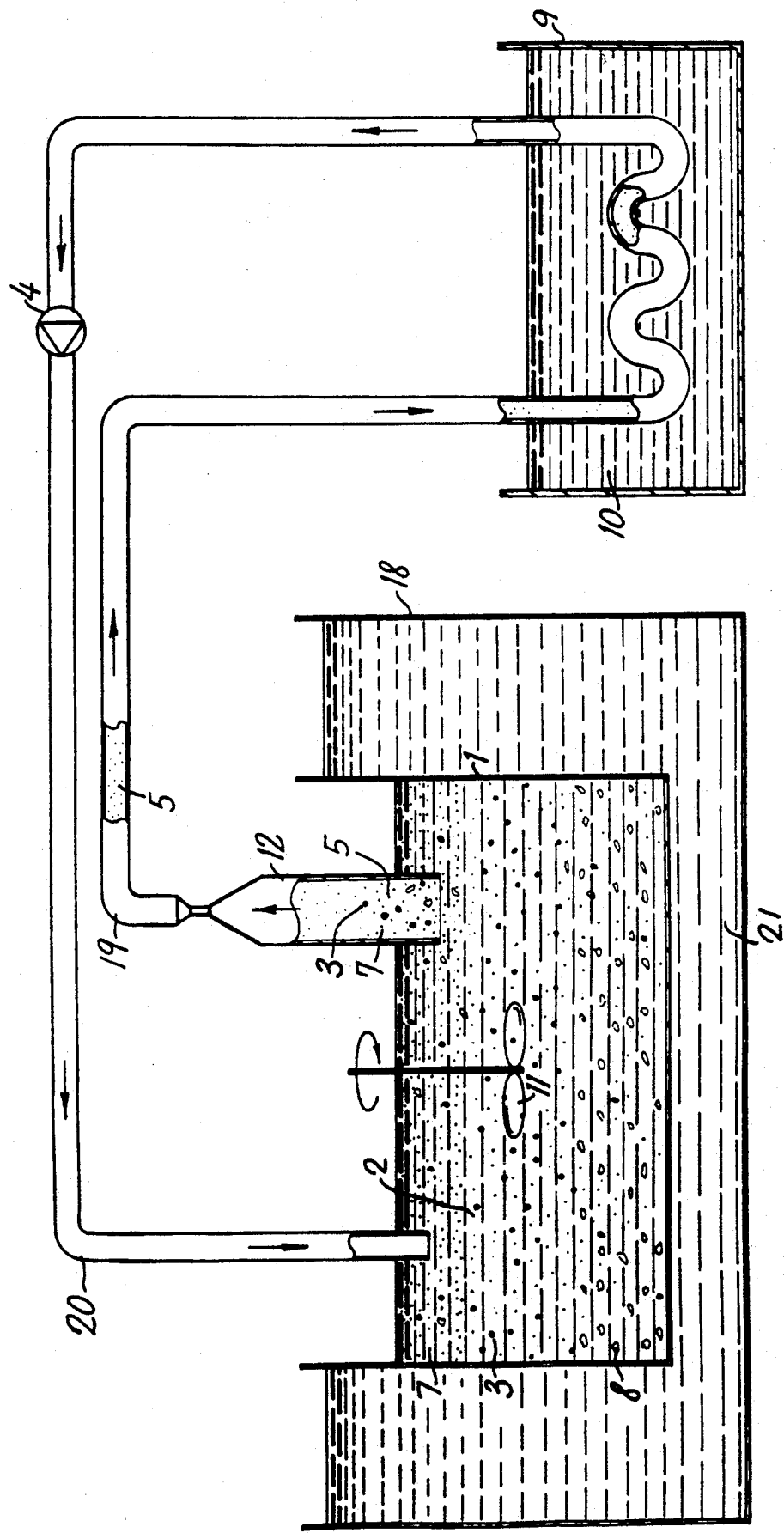
FIG. 2 is a schematic diagram reflecting another embodiment of the process of the invention.

With reference to the drawings, particularly FIGS. 1 and 2, there is shown a crystallization chamber 1 which may be a simple cylindrical beaker or container. The chamber contains a saturated solution or fine suspension of a crystallizable enzyme 2. The crystallization chamber 1 (crystallizer) is provided with a stirrer 11 and is cooled, preferably with a cooling jacket 18 containing a heat transfer medium 21, to maintain a selected temperature at which crystals 3 will form. As the crystals are forming, a liquid stream 5 is continuously drawn, aided by a pump 4, from the crystallizer 1 through a classification device 6. This device may be a sieve (FIG. 1) or simple wide bore tube, sedimenter 12 (FIG. 2) or hydrocyclone or any other device conventionally used to classify solid particles suspended in a liquid. The effect of the classification device 6 is to allow small crystals 7 to pass through while relatively large crystals 8 are held back. The separated liquid containing relatively small crystals travels through a tube 19 to a heat exchanger 9, where it is heated so as to dissolve a substantial portion or all of the crystals 7 in the liquid. As shown, the heat exchanger 9 is a simple temperature controlled bath wherein the transfer of heat between both liquid 10 and the enzyme containing stream 5 is sufficient to melt the enzyme. The liquid containing dissolved enzyme is then recycled back through a tube 20 to the crystallizer 1 where its temperature is immediately lowered upon mixing into the batch with the aid of a stirrer 11. New crystals are formed, some of which grow on the previously existing crystals 8 held back by the classification device 6. Using this procedure, a high degree of supersaturation is continuously maintained until all of the crystallizable enzyme is deposited onto the select group of relatively large crystals which were not permitted to leave the chamber 1.

The process as described can be used for a wide variety of crystallizable enzymes, for example glucose isomerase, horse radish peroxidase, barley beta amylase, lysozyme from hen egg white, alpha amylase from porcine pancreas, hemoglobin, and aldolase of rabbit skeletal muscle.

Optionally, certain salts such as ammonium or magnesium sulfate may be employed initially or during the crystallization process to decrease the solubility and induce crystallization of the enzyme. A good example of an enzyme for which this procedure is applicable is glucose isomerase. In studies using glucose isomerase, it has been determined that the crystals have a solubility minimum at a magnesium sulfate concentration of around 1.5%. The solubility of glucose isomerase increases when the magnesium sulfate concentration is increased above the minimum. Using ammonium sulfate, on the other hand, the solubility of glucose isomerase decreases with increasing salt concentration according to the well known general salting out formula for proteins, $\log S = A + (B)(I)$ where S is the solubility, A and B are constants which depend on the enzyme and I is the ionic strength of the medium (directly proportional to the salt concentration).

At all magnesium and ammonium sulfate concentrations the solubility is higher at higher temperatures. Thus, the heating procedure is applicable to dissolve the small crystals in the process according to the invention.

The salt used to induce crystallization, as well as the optimum concentration of the salt, will vary depending on the nature of the enzyme. Further, the choice of salt may depend on the post crystallization treatment that will be used on the crystalline product. In cases where the crystals will be crosslinked using, for example, glutaraldehyde, ammonium sulfate is in some cases preferred as the ammonium ions participate in the crosslinking. (See copending U.S. application Ser. No. 350,720 which is incorporated by reference herein.)

The seed crystals which serve as nucleation sites for the growth of crystals according to the invention can be produced by any known enzyme precipitation or crystallization method known in the art, such as the "salting out" methods described above. However, it is also possible to have previously prepared seed crystals for use in the start-up of the present process. Such seed crystals may have been produced in previous crystallizations carried out using the method disolosed herein. Alternatively, seed crystals may be created initially by gradually adding solubilized enzyme as an independent feed to a cooled saturated solution until enough crystals are built which are of sufficient size to act as the seed crystals in the process of this invention. This may be a separate operation outside the crystallization chamber of this invention.

The size of the relatively small particles to be re-dissolved and recycled is a matter of choice. It is evident that the smaller the number of crystals kept in the growing chamber, the larger the crystals must be at the solubility equilibrium. Thus, in order to grow relatively large enzyme crystals, the number of initial (seed) crystals kept in the growing chamber and not re-dissolved should be kept fairly low. This will allow the remaining enzyme matter during recycling to deposit on relatively few seed crystals, thus leading ultimately to relatively few larger crystals. In practice it is very difficult to determine the number of crystals present in the crystallized enzyme batch. The procedure according to the invention will, however, rapidly reduce the number of the initial crystals, regardless of their number. The ultimate size of the crystals will be determined by the dimensions of the apparatus, the circulation rate, the total quantity of the enzyme, and the screening capability of the classification device. When using a sieve, the mesh size is obviously determinative. When using a wide bore sedimenter 12 as shown in FIG. 2, the dimensions of the tube (width and height), for a given flow rate, are determinative. The flow rate is established to prevent the relatively large (and heavier) crystals from being lifted into stream 5.

The rate at which the suspended relatively small particles are removed, re-dissolved and returned to the growing chamber is fairly independent of the growing process itself and is usually limited by mass transfer and heat transfer considerations. Within the constraints of mass transfer and heat transfer, the more quickly the relatively small particles are removed, dissolved and returned, the more quickly the larger crystals grow.

The dimensions of the equipment, stirrer speed and rate of circulation ultimately influence the size of the crystals produced. The final average size of the crystals is a continuous function of stirring speed when the rate of circulation through the classification device is kept constant. Increasing the rate tends to increase the final size of crystals.

The conditions selected will depend on the nature of the enzyme or macromolecule crystallized. Although the conditions described in the preferred method below are particularly suitable for glucose isomerase, the principle of the process is applicable to any crystallizable protein. The conditions for other enzymes will need to be adjusted to take into account the particular solubility and crystallizability characteristics of such enzymes, all of which are well known or easily established. Regardless of the enzyme to be crystallized, it is essential that the solubility characteristics of the enzyme at various temperatures be taken into consideration in designing a system to circulate the enzyme under conditions where its solubility is increased. In certain cases, the dissolving temperature may be lower than the crystallization temperature if the solubility of the protein in question is lowered at increased temperature. The type or amount of agent used to decrease the solubility of the enzyme in the crystallizing chamber is not critical.

In the preferred method for crystallizing glucose isomerase, the concentration of enzyme is about 1 to about 400 g protein per liter and most preferably about 50 to about 200 g protein per liter. The enzyme concentration can vary from 1–400 g protein per liter. Ammonium sulfate is added at a level of about 20-150 g per 1000 g of mixture with about a 10% concentration being preferred. The temperature of the crystallizer is maintained at about 6° to 25° C. and most preferably about 8°-20° C. The dissolving temperature is from about 25° to 60° C. and is most preferably about 40°-50° C. (or anything above the crystallizer temperature). The circulation flux, stirring and dimensions may be varied widely. Generally, the rate of circulation is about one to four crystallizer batch volumes per hour.

Figure 3:
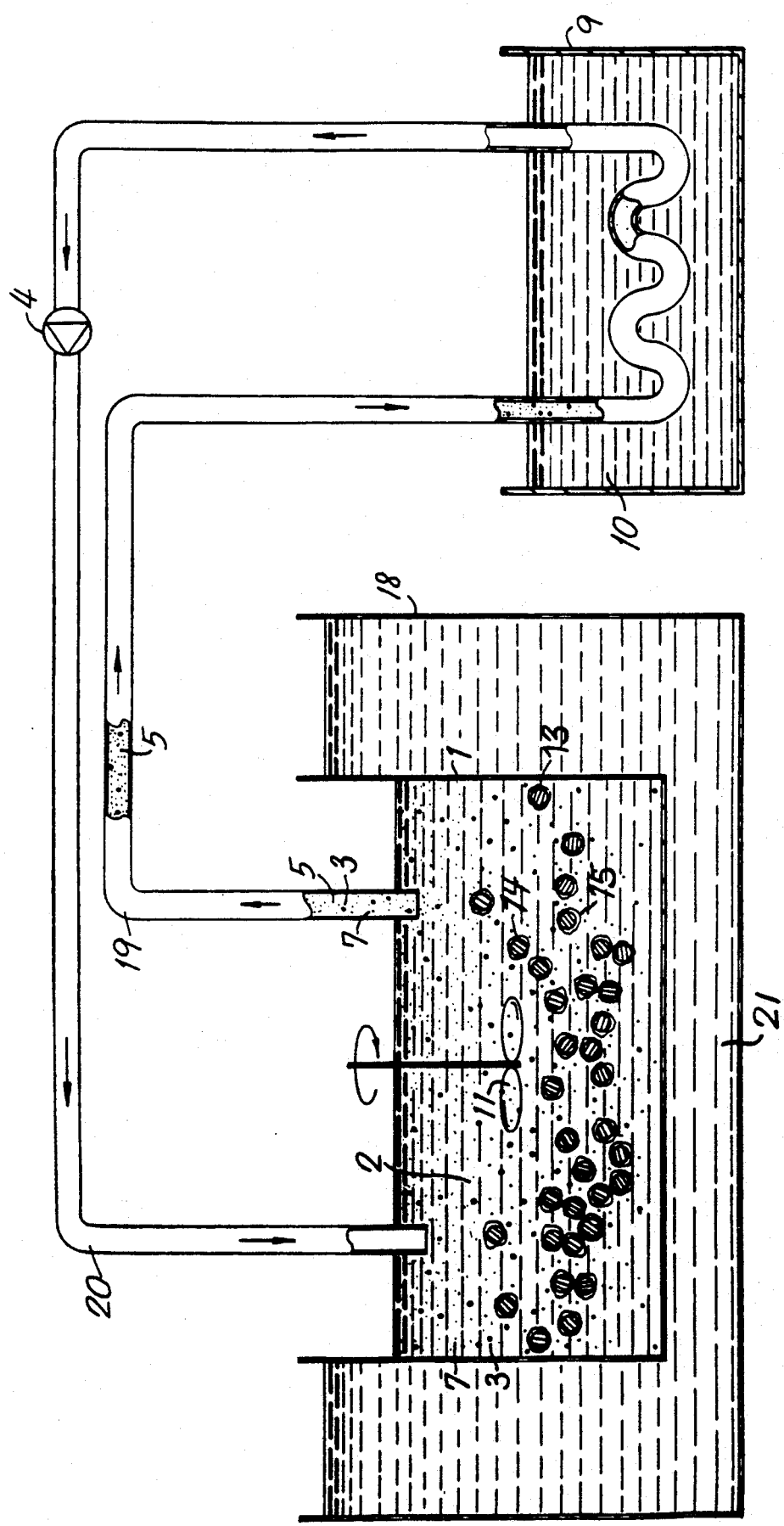
FIG. 3 is a schematic diagram depicting yet another embodiment of the process of the invention.

A further embodiment of the invention is illustrated in FIG. 3. In this embodiment, the chamber 1 contains an insoluble solid material, such as beads 13, which provide surfaces 14 on which the crystallizing enzyme 15 may deposit. During the process, the surface of the insoluble solid material appears to provide nucleation sites for deposition of enzyme. As the process proceeds, a coating of crystallized enzyme is built up on the surface of the solid material. Enzyme layers of any desired thickness may be grown in this manner. As shown, the solid material is a bead or sphere, but any shape is suitable For example, the solid material may be in the form of sheets, grids or fabric. It may be composed of any suitable insoluble material which is unaffected (inert) under the conditions of the process. For example, glass, steel, high polymers (e.g., polystyrene, polyacrylics, teflon, polyamides, polyethylene, polypropylene, and the like), ion exchange resins and celluosics are all suitable.

It is convenient to have the insoluble solid material removable from the chamber for recovery of the coated enzyme. For this purpose, loose beads are particularly preferred. It is also contemplated, however, that the solid material can also be fixed or removably fixed within the chamber. In this event, it is not necessary to provide a classification device to separate the growing crystal mass from the smaller crystals which form elsewhere in the chamber. Beads, depending on their weight and size, may also avoid the necessity of a classification device.

Once the enzyme has been deposited on the solid surface, it may be fixed by any method applicable for the particular enzyme. For example, it can be cross-linked with glutaraldehyde. The composite thus formed may be further coated or encapsulated if desired.

In the most preferred method, the following general parameters are used:

Enzyme solution, containing between 2 and about 100 grams per liter of enzyme is held in a crystallizing chamber at a temperature of between about 2° and about 7° C. Ammonium sulfate (5-15% by weight) or magnesium sulfate (about 1-5% by weight) may be added to the solution. The material to be coated is either dropped in as freely moving particles or as a fixed object in the crystallizing chamber.

The crystallizing chamber is constantly stirred, and the small crystal containing solution continuously withdrawn and passed through a heat exchanger, which raises the temperature of the solution to from about 30° to about 50° C., thereby dissolving the small enzyme crystals. The solution is then returned to the crystallizing chamber, wherein its addition acts to maintain the supersaturation of the crystallizing solution. The preferred rate of circulation through the heat exchanger is about 1 to about 6 batch volumes per hour. Most preferably, the small crystal containing liquid is removed by passage through a sieve that has a mesh which is the largest possible to retain the free particles to be coated.

The principle of the invention can be used to produce crystals from a wide variety of enzymes. Because glucose isomerase is particularly suitable for the process described herein, it was used as a model in the Examples described below. The examples, though not limiting of the invention, are illustrative of it.

EXAMPLES

Examples 1-3 were performed in 0.5-10 liter batches. A total of approximately 0.1-5 kilograms (wet basis) of large (0.5 to 1.0 mm) diameter crystals of glucose isomerase were produced. There is no definable upper or lower scale limit for the process. It is adaptable to both a few milliliter laboratory scale and to a cubic meter size industrial process.

EXAMPLE 1

Preparation of the Starting Material

Glucose isomerase concentrate was prepared as described in U.S. Pat. No. 4,410,627 as follows: *Streptomyces rubiginosus* was fermented in a 36 cubic meter batch fermentation. The cell mass in the batch was lysed to release the intracellular isomerase. The cell debris was filtered to recover the clear enzyme containing solution. The solution was ultrafiltered and the enzyme containing retentate, typically 1.6 cubic meters, was used as the isomerase containing concentrate in the example processes. Aliquots of the concentrate were used in the various examples. Part of the concentrate was crystallized as described in the prior art (see U.S. Pat. No. 4,604,199) and the crystals were further used in some examples briefly described as follows:

10 percent by weight of ammonium sulfate was added to the concentrate. Glucose isomerase was crystallized as a heterogeneous crystal family. The product contained all crystal sizes between 1 and 50 micrometers.

The crystals were recovered as viscous solid sediment by centrifugation. This sediment was used as a starting material in some examples.

EXAMPLE 2

Crystal Growing Procedure 1.8 liters of glucose isomerase concentrate containing 36 grams of isomerase protein (approximately 1.4 million GIU of glucose isomerase activity units) was placed in the crystallizer (diameter 150 cm, height 170 cm). Stirring with the impeller was started and maintained at 100 RPM during the whole procedure. Ammonium sulfate (0.2 kg) was added and dissolved. The crystallizer was cooled with an outside water bath having a temperature of 10° C. The pump was started and the flow rate was adjusted to 4 liters per hour. The crystallizing mixture was allowed to flow through a cylindrical sedimenter tube having a diameter of 4.5 cm and a height of 18 cm. The mixture was then passed through a heat exchanger immersed in a water bath having a temperature of 50° C. The internal volume of the heat exchanger tube was 39 ml and its diameter was 4 mm. The crystals were dissolved in the heat exchanger and the solution was returned to the crystallizer.

At the beginning, the crystals appearing in the crystallizer were all sizes below 50 micrometers. A high degree of supersaturation was maintained by the continuous dissolving and circulation through the heat exchanger. The supersaturation facilitated continuous growth of all crystals remaining in the crystallizer. However, proportionally more of the smallest crystals travelled through the sedimenter tube and were dissolved. The larger the crystals were, the less likely it was that they would travel through the dissolving circuit. It was observed that the largest crystals could have a sedimentation velocity higher than the linear flow velocity in the sedimenter tube. Such crystals could practically never enter into the dissolving heat exchanger.

When this procedure was maintained, the following was observed. The average size of the crystals grew continuously.

During the first 3-4 hours they typically grew 50 micrometers per hour. The small (1-50 micrometers) crystals which were numerous at the beginning, disappeared to a very small, practically negligible quantity towards the end of the procedure. As can be seen in Table 1 below, after 25 hours, more than 95% of the glucose isomerase was in crystals having a diameter of 700-1200 micrometers. The crystal growth practically ceased when the size of the crystals was so large that only negligible amounts of crystals passed through the heat exchanger. It is evident that at the end of the process, all of the crystallized isomerase was in the large crystals.

After 25 hours, the pumping and stirring were terminated. The crystals were allowed to sediment in the crystallizer. After 30 minutes, the mother liquor was removed by decantation. The weight of the solid, water containing isomerase crystal sediment was 100 grams. More than 95% of the original isomerase was in the crystal sediment.

TABLE 1

CRYSTAL GROWTH IN EXAMPLE 1

| Hours | Crystal Diameter In Micrometers |
|-------|---------------------------------|
| 1     | 0-300                           |
| 4     | 200-600                         |
| 8     | 400-800                         |
| 20    | 600-1000                        |
| 25    | 700-1100                        |

EXAMPLE 2

Crystallization Process at Higher Temperature and Higher Crystal Density

This experiment was performed with the same equipment as in Example 1. 530 grams of glucose isomerase crystal sediment were mixed with 1350 grams of tap water in the crystallizer. The mixture was heated to a temperature of 27° C. by circulating through the heat exchanger and stirring until all the isomerase crystals were dissolved. The crystallizer was not cooled during this procedure, which was completed in 40 minutes. 150 grams of ammonium sulfate was dissolved in the solution to bring the concentration to 10%.

The crystallizer was cooled to 18° C. with a water bath. The solution was pumped at a flow rate of 7 liters per hour though the heat exchanger in a 50° C. water bath. The solution in the crystallizer had a temperature of 21° C. because of the warming effect of the solution coming from the heater.

The crystallization started immediately when the temperature in the crystallizer was lowered to 21° C. The crystals grew very rapidly at the beginning; the largest crystals had a diameter of 300 micrometers after 1 hour. The growth rate decreased rapidly once the isomerase was transformed to large crystals. After 20 hours, most of the crystals had a diameter of between about 500 and 900 micrometers. The large crystals were recovered by decantation after 30 minutes settling as in Example 1. The weight of the crystal sediment was 400 grams, which is a 75% yield on the crystal weight basis. Most of the non-recovered isomerase was soluble in the mother liquor because of the relatively high temperature used in this example. (The isomerase in the mother liquor was recovered by cooling and recrystallization).

EXAMPLE 3

The principle of the equipment was mostly the same as in example 1, but the dimensions were different. The crystallizer was a 20 liter polyethylene container. It was cooled by outside cold air at a temperature of 2° C. The solution in the crystallizer was gently stirred with an impeller so as to produce a slowly rotating motion of the liquid. The solution was taken through a simple 4 mm diameter tube from the surface close to the axis of the stirrer and pumped through the heating coil in a 47° C. water bath. After heating, the solution was passed through a cooling coil in a 10° C. water bath. The cooled solution was returned to the crystallizer.

A 6.2 kilogram portion of glucose isomerase crystal sediment was used in the process. 12.5 kilograms of 10% ammonium sulfate solution was added and stirred in the crystallizer to produce a homogeneous suspension. The stirring speed used throughout the process was 180 RPM and the impeller was adjusted to a height 1 cm from the bottom. The solution was pumped at a rate of 5 liters per hour through the heat exchangers. The temperature in the crystallizer was 12° C.

The crystals originating from the industrial scale recovery process described in Example 1 had sizes from 1 to 100 micrometers. Practically none of the crystals were dissolved in the beginning of this procedure. However, as the solution was taken from the surface and center of the crystallizer, the smaller crystals disappeared gradually. The crystallizer container itself served as a sedimenter device. It could be observed that the smaller crystals were preferably following the liquid flow through the dissolving circuit. The separating effect was improved with the rotating motion of the liquid.

This process was maintained for 120 hours. At the end, all of the isomerase was crystallized in a very narrow size distribution; the crystals had diameters of 150–210 micrometers. No smaller crystals were observed. The crystals were allowed to sediment and the mother liquor was removed by decantation. The weight of the recovered crystals was 6.1 kg.

EXAMPLE 4

500 grams of glucose isomerase crystals (containing 36% enzyme protein and 64% water) were mixed with 2000 ml of 10% ammonium sulfate solution. The mixture was placed into the crystallizer. The suspension was stirred with a stainless steel propeller having three blades and a diameter of 11 cm. The temperature in the crystallizer was kept at 16° C. by an outside cooling bath held at a temperature 8° C. The suspension was pumped through the heat exchanger immersed in a 50° C. water bath. The flow rate was 3 liters per hour. The procedure was continued for 24 hours. The crystal containing solution was poured away and used for other experiments.

The propeller was covered with a transparent layer of crystalline isomerase. The weight of the layer was about 3 grams. The enzyme layer was crosslinked by immersion into a solution of glutaraldehyde in 10% ammonium sulfate at 4° C. for 4 hours. The crosslinked enzyme layer was well fixed on the propeller. The enzymatic activity of the enzyme-coated propeller was demonstrated by stirring in a 400 ml sample of 10% glucose with it. After 1 hour stirring at 40° C. the fructose content of the sample was approximately 4%.

EXAMPLE 5

The same equipment was used as in Example 4. 530 grams of glucose isomerase crystals (wet basis, 60% water) was placed in the crystallizer. 1350 grams of water was added and the mixture was stirred continuously and heated 30° C. until all of the crystals were dissolved. 150 grams of ammonium sulfate were added and stirred until dissolved. The temperature in the crystallizer was then lowered and maintained at 23° C. with an outside cooling bath. The enzyme solution was pumped with a flow rate of 8 liters per hour through the heat exchanger immersed in a 50° C. water bath. All of the crystals which passed through the heat exchanger were dissolved. The stirrer was kept on at 100 RPM throughout the process.

The process was continued 25 hours, at which time the contents of the crystallizer were poured aside. The crystallizer was wiped to remove all of the loose liquid and weighed. The inside walls of the crystallizer were coated with a glassy layer of crystalline glucose isomerase. Subtracting the tare weight of the crystallizer, the weight of the enzyme layer was calculated to be 39 grams of wet crystal.

The enzyme layer was fixed by crosslinking as follows. The crystallizer was filled with 2 liters of ice cold (1° C.) 10% ammonium sulfate which was previously saturated with glucose isomerase crystals to prevent the dissolving of the isomerase layer. 50 milliliters of 50% glutaraldehyde was added and the mixture was stirred 3 hours to allow the crosslinking to occur. After crosslinking the crystallizer was emptied and washed with water until all solubles were removed. The isomerase was now a glassy yellowish brown layer on the walls of the stainless steel vessel.

The enzymatic activity of the layer was demonstrated by filling the crystallizer with 2 liters of 30% glucose solution at pH 7.5. The solution was stirred at 60° C. for 3 hours. Samples were taken from the solution and assayed for fructose. A continuous increase of fructose content was observed. At 3 hours, the fructose concentration was 13% and the glucose concentration was 17%.

EXAMPLE 6

300 grams of glucose isomerase crystals (wet basis as before) were dissolved in 1000 ml of 12% ammonium sulfate solution by heating to 35° C. 50 g of glass beads, diameter 300–500 micrometers (average 400), were added. The mixture was stirred in the crystallizer with the propeller at 120 rpm to prevent the sedimentation of the beads. The suspension was cooled to a temperature of 20° C. to start the crystallization.

The solution was circulated with a flow rate of 1 liter per hour through the sieve and the heater immersed in a 50° C. water bath. All of the free crystals were dissolved in the heater. The process was maintained for 18 hours. The glass beads were coated with a 100 micrometer layer of crystalline glucose isomerase.

This example demonstrated that the enzyme is able to crystallize on glass surface. However, it was observed that the enzyme layer was not mechanically as stable as in the other examples. In prolonged stirring, the enzyme layer was released from the beads.

EXAMPLE 7

550 grams of glucose isomerase crystals (wet basis) were mixed with 2000 ml of a 10% ammonium sulfate solution in the crystallizer. 100 grams (130 ml packed bed volume) of composite spherical beads were added. The beads had the following structure:
  diameter 500–800 micrometers
  core sphere made of polystyrene and wax melted together
  surface layer of short fiber native cellulose glued on the core with dissolved polystyrene
  cellulose content 20% by weight
  fiber length of the cellulose, less than 50 micrometers.

The mixture was stirred at 100 RPM throughout the process. The temperature was adjusted to 16° C. at the beginning and lowered gradually to 11° C. at the end of the process. The solution was pumped beginning at a flow rate of 7 liters and ending with a flow rate of 3 liters per hour through the sieve (the flow rate was reduced gradually) and the heat exchanger immersed in a 50° C. water bath. The total time of the procedure was 47 hours. At the end, most of the isomerase was layered on the beads as an almost perfect spherical layer. The sharp edges of the enzyme crystals layered on the composite beads were continuously worn down in the procedure, resulting in a relatively smooth spherical surface. However, at large magnification (100× or more) in a light or scanning electron microscope it could be observed that the surface of the sphere was covered throughout with the typical crystal faces of glucose isomerase. The glassy transparency of the enzyme coating was also evidence of the crystalline nature of the layer.

The enzyme was fixed on the spheres by crosslinking as follows:

1100 ml of the mother liquor was poured away to make a more dense suspension. The temperature of the mixture was kept at 4° C. throughout the crosslinking process. 120 grams of lysine hydrochloride was added and dissolved by stirring. 1 mole of dipotassium hydrogen phosphate was added to keep the pH between 6 and 8 throughout the process. 250 ml of 50% glutaraldehyde were added. The mixture was stirred 3.5 hours. The mother liquor was poured away and the product was washed with water on a standard sieve with 500 micrometers mesh until all visible colored liquid and small particles were removed. The spherical product particles were drained on the sieve until no more water was removed. The weight of the product was 550 g and the sedimented bulk volume 400 ml. The product appeared as very uniform brown spheres. The diameter of 95% of the particles was between 900 and 1100 micrometers. It appeared that the smaller composite particles were coated with thicker layers and the larger ones with thinner layer of isomerase. Thus the size distribution of the product was narrower than that of the original core particles.

The enzymatic activity of the product was demonstrated by stirring a 5 gram sample of the product with 100 ml of 40% glucose at 60° C. The fructose content of the mixture increased up to 18% within 2 hours.

EXAMPLE 8

100 grams of composite carrier was used as nuclei to be coated. The carrier had the following composition and shape:

25% fibrous wood cellulose
25% titanium dioxide
50% polystyrene as adhesive
particle size 350–850 micrometers
shape of the particles was irregular
this material is described in U.S. Pat. No. 4,355,117, Example 1 (the granulate was not, however, derivatized with diethyl amino ethyl chloride hydrochloride)

200 grams of glucose isomerase crystals (wet basis) and 1800 ml of 10% ammonium sulfate was mixed with the carrier in the crystallizer. The mixture was stirred at 100 rpm throughout the process. The liquid was pumped with a flow rate of 2 liters per hour through the screen and heat exchanger in a 50° C. water bath. The temperature in the crystallizer was kept at 8° C.

The process was stopped after 24 hours. The contents of the crystallizer was poured on a 300 micrometers sieve and drained to remove the mother liquor. The product on the sieve was analyzed for glucose isomerase. The product contained 150 grams of crystalline isomerase coated on the carrier and the remaining 50 grams of enzyme were in the mother liquor which drained through the sieve. As observed under a microscope, the enzyme appeared as a glassy transparent layer on the dark non-transparent carrier particle. The enzyme was fixed on the particles by crosslinking with glutaraldehyde. The enzymatic activity was demonstrated by mixing with glucose and observing the conversion to fructose.

EXAMPLE 9

Crystallization Procedure in Magnesium Sulfate Medium

Glucose isomerase concentrate was prepared described in Example 1. 28 grams of magnesium sulfate (calculated as dry substance) were added and dissolved in 1 liter of the concentrate at a temperature of 25° C. The mixture was stirred continuously and cooled to a temperature of 5° C. Glucose isomerase was rapidly crystallized and after 3 hours, 97% of the original activity was in the crystals and 3% of the activity was still in the mother liquor. No other materials were precipitated or crystallized. The crystalline isomerase was recovered by centrifugation as described in Example 1. This crystal sediment was used as starting material in the magnesium sulfate medium examples.

Crystal Growing Procedure

The apparatus of FIG. 2 was used in the procedure. 1 kg of glucose isomerase crystals was suspended into 5 liters of 2% magnesium sulfate solution. The small crystals were circulated through a heating coil immersed in a water bath held at a temperature of 50° C. The circulation rate was 15 liters per hour. The crystallizer was kept at a temperature of 16° C. The procedure was continued for 20 hours. Practically all of the crystals were in the size class of 500–700 micrometers after this procedure.

EXAMPLE 10

Crystal Coating Procedure

The apparatus of FIG. 1 was used in the procedure. The reaction mixture in the crystallizer was as follows:
3.4 kg of glucose isomerase crystals
3.9 kg of composite carrier as described in Example 8
15 liters of 2% magnesium sulfate The crystallizer was maintained at a temperature of 16° C. The mother liquor containing free isomerase crystals was circulated through a heating coil immersed in a water bath held at 50° C. Within 24 hours, 80% of the isomerase protein was deposited as a crystalline layer on the carrier. The mother liquor was removed by decantation. The enzyme coated material was subjected to a crosslinking procedure to fix the enzyme on the carrier. The protein content of the final crosslinked product was 21%. The product was enzymatically active when tested as in Example 7.

Examples 9 and 10 demonstrate that the procedure works in different media. It follows that all of the chemical and physical conditions which decrease the solubility of enzymes can be adjusted to work in the invented procedure.

Many obvious variations of the invention disclosed will suggest themselves to those skilled in the art. Nothing in the preceding specification is intended, however, to limit the scope of the invention as defined by the following claims.

I claim:

1. A process for producing crystalline glucose isomerase having a crystal size of from about 0.5 to 1 mm, comprising maintaining a solution of crystallizable glucose isomerase at a sufficiently cool temperature to induce crystal formation, separating from the solution a liquid stream containing glucose isomerase crystals smaller than 0.5 mm, heating said liquid to substantially dissolve the crystals, and returning the liquid with dissolved glucose isomerase to said solution cooled to maintain said solution in a supersaturated condition for further crystallization.

2. A process according to claim 1 wherein the solution of crystallizable glucose isomerase is maintained at a temperature of from about 2° C. to about 25° C.

3. A process according to claim 1 wherein said crystallizing solution contains about 1 to about 400 grams of protein per liter.

4. A process according to claim 1 wherein the heating temperature is from about 25° C. to about 60° C.

5. A process according to claim 1 wherein an enzyme solubility decreasing agent is added to said supersaturated glucose isomerase solution.

6. A process according to claim 5 wherein said agent is salt.

7. A process according to claim 6 wherein said salt is magnesium sulfate or ammonium sulfate.

8. A process for growing crystalline glucose isomerase having a crystal size of from about 0.5 to 1 mm comprising:
   (1) loading a crystal growing chamber with a saturated solution or fine suspension of a crystallizable glucose isomerase;
   (2) maintaining the temperature of the solution or suspension in the crystal growing chamber sufficiently low to induce crystal formation;
   (3) separating crystals of less than 0.5 mm from the solution by continuously passing a portion of the cooled liquid containing suspended crystals from the crystal forming chamber through a size classification means whereby the crystals of less than 0.5 mm are removed from the chamber in a liquid stream and the remaining crystals are retained in the chamber;
   (4) heating the stream containing glucose isomerase crystals of less than 0.5 mm sufficiently to substantially dissolve the crystals suspended therein;
   (5) returning the heated stream with dissolved glucose isomerase back to the crystal growing chamber so as to maintain the liquid in the chamber in a supersaturated condition;
   (6) continuing the above process steps (2) through (5) until the crystals in the crystal growing chamber have grown to between about 0.5 mm and 1.0 mm; and
   (7) recovering the crystals of glucose isomerase so grown.

9. A process according to claim 8 wherein the temperature of the crystallizing chamber is about 8° C. to about 20° C.

10. A process according to claim 8 wherein the crystallizing solution contains 50 to about 200 grams of protein per liter.

11. A process according to claim 8 wherein the heating temperature is between about 30° C. and about 50° C.

12. A process according to claim 8 wherein a salt is added to said saturated solution or fine suspension to decrease the solubility of said crystallizable glucose isomerase.

13. A process according to claim 12 wherein said salt is magnesium sulfate or ammonium sulfate.

14. A process according to claim 13 wherein ammonium sulfate is added at a concentration of about 5 to about 15% by weight to the crystallizing solution.

15. A process according to claim 13 wherein magnesium sulfate is added at a concentration of about 1 to about 5% by weight to the crystallizing solution.

16. A process for growing glucose isomerase crystals having a size of from about 0.5 to 1 mm on a solid carrier comprising:
   (1) placing an insoluble, inert material in a crystal growing chamber containing a saturated solution or fine suspension of a crystallizable glucose isomerase;
   (2) maintaining the temperature of the solution in the crystal growing chamber sufficiently low to induce the formation of crystals, a portion of which are deposited on the surface of said inert material and another portion of which exist as free crystals having a crystal size of less than 0.5 mm;
   (3) continuously removing in a liquid stream the free crystals from the crystal growing chamber;
   (4) heating the stream to substantially dissolve the crystals suspended therein;
   (5) returning the liquid stream with dissolved crystals to the crystal growing chamber so as to maintain the solution in a supersaturated state;
   (6) continuing the above process steps (2) through (5) until the solid material is sufficiently coated; and
   (7) removing the solid material.

17. A process according to claim 16 wherein the inert material is made of glass, stainless steel, cellulose, teflon, ion-exchange resin, or plastic.

18. A process according to claim 16 wherein the crystal growing chamber is maintained at a temperature of from about 2° to about 7° C.

19. A process according to claim 16 wherein the saturated solution or fine suspension contains about 2 to about 100 grams of protein per liter.

20. A process according to claim 16 wherein said heating is between about 30° C. and 50° C.

21. A process according to claim 16 wherein a salt is added to said saturated solution or fine suspension to decrease the solubility of said crystallizable glucose isomerase.

22. A process according to claim 21 wherein said salt is ammonium or magnesium sulfate.

23. A process according to claim 22 wherein magnesium sulfate is added at a concentration of 1–5% by weight to the solution.

24. A process according to claim 22 wherein ammonium sulfate is added at a concentration of 5–15% by weight to the solution.

* * * * *